United States Patent
Lee et al.

(10) Patent No.: US 10,085,941 B2
(45) Date of Patent: Oct. 2, 2018

(54) PHARMACEUTICAL COMPOSITION FOR PARENTERAL ADMINISTRATION, CONTAINING DONEPEZIL

(71) Applicant: DONGKOOK PHARMACEUTICAL CO., LTD., Gyeonggi-do (KR)

(72) Inventors: Deok Keun Lee, Seoul (KR); Sung Jin Ko, Gyeonggi-do (KR); Shin Eom, Gyeonggi-do (KR); Kyung Hoi Cha, Gyeonggi-do (KR)

(73) Assignee: DONGKOOK PHARMACEUTICAL CO., LTD., Gyeonggi-do (KR)

( * ) Notice: Subject to any disclaimer, the term of this patent is extended or adjusted under 35 U.S.C. 154(b) by 0 days.

(21) Appl. No.: 14/782,276

(22) PCT Filed: Apr. 2, 2014

(86) PCT No.: PCT/KR2014/002844
§ 371 (c)(1),
(2) Date: Oct. 2, 2015

(87) PCT Pub. No.: WO2014/163400
PCT Pub. Date: Oct. 9, 2014

(65) Prior Publication Data
US 2016/0022583 A1    Jan. 28, 2016

(30) Foreign Application Priority Data

Apr. 3, 2013 (KR) .................. 10-2013-0036292

(51) Int. Cl.
*A61K 9/16* (2006.01)
*A61K 31/445* (2006.01)
*A61K 9/00* (2006.01)

(52) U.S. Cl.
CPC .......... *A61K 9/1647* (2013.01); *A61K 9/0019* (2013.01); *A61K 9/0073* (2013.01); *A61K 9/1682* (2013.01); *A61K 31/445* (2013.01)

(58) Field of Classification Search
CPC .. A61K 9/0073; A61K 9/1647; A61K 9/1682; A61K 9/0019; A61K 31/445
See application file for complete search history.

(56) References Cited

U.S. PATENT DOCUMENTS

| | | | |
|---|---|---|---|
| 7,429,559 B2 | 9/2008 | Yamamoto et al. | 514/2 |
| 8,840,922 B2 | 9/2014 | Kawakami et al. | 424/449 |
| 2007/0059369 A1* | 3/2007 | Mauvernay | A61K 9/0024 424/486 |
| 2010/0015195 A1* | 1/2010 | Jain | A61K 9/0024 424/422 |
| 2012/0121711 A1 | 5/2012 | Hu et al. | |
| 2013/0224257 A1 | 8/2013 | Sah et al. | 424/400 |

FOREIGN PATENT DOCUMENTS

| | | | |
|---|---|---|---|
| EP | 2460539 | 6/2012 | A61K 47/34 |
| JP | H10-203966 A | 8/1998 | |
| JP | 2013-500944 A | 1/2013 | |
| KR | 10-0961413 | 5/2010 | A61K 47/34 |
| KR | 10-2010-0094227 | 8/2010 | A61K 9/16 |
| KR | 10-2012-0011344 | 2/2012 | A61K 9/14 |
| KR | 10-2012-0093293 | 8/2012 | A61K 9/70 |
| KR | 10-2012-0122558 | 11/2012 | A61K 31/445 |
| WO | WO 2008/041245 | 4/2008 | A61K 9/16 |
| WO | WO 2012/148225 | 11/2012 | A61K 31/445 |
| WO | WO 2013/005094 | 1/2013 | C07D 211/32 |
| WO | WO 2013005094 A1 * | 1/2013 | A61K 9/0019 |

OTHER PUBLICATIONS

Supplementary European Search Report dated Jul. 13, 2016 in EP 14779696.
Bhavna, et al. (2014) "Preparation, characterization, in vivo biodistribution and pharmacokinetic studies of donepezil-loaded PLGA nanoparticles for brain targeting." *Drug Dev. Ind. Pharm.* 40(2):278-287.
Zhang, et al. (2007) "In vitro and in vivo evaluation of donepezil-sustained release microparticles for the treatment of Alzheimer's disease." *Biomaterials* 28:1882-1888.
International Search Report (ISR) dated Jul. 17, 2014 in PCT/KR2014/002844 published as WO 2014/163400 with English Translation.

* cited by examiner

*Primary Examiner* — Doan T Phan
(74) *Attorney, Agent, or Firm* — Harness, Dickey & Pierce, P.L.C.

(57) ABSTRACT

The present invention relates to a composition for parenteral administration, containing donepezil as an active ingredient, and a preparation method therefor. Donepezil, which has been conventionally used for oral or transdermal administration, is prepared as microparticles comprising a biodegradable and biocompatible polymer and a release controller so as to be provided as a pharmaceutical composition for sustained release parenteral administration, thereby enabling in vivo sustained release continuously for 2-12 weeks or more. Therefore, it is possible to reduce the frequency of administration to a patient and maintain an effective concentration in the blood for a long time.

11 Claims, 10 Drawing Sheets

EXAMPLE 1

EXAMPLE 1-1

EXAMPLE 2

EXAMPLE 3

EXAMPLE 4

EXAMPLE 5

EXAMPLE 6

EXAMPLE 7

EXAMPLE 2-1

EXAMPLE 8

EXAMPLE 8-1

EXAMPLE 9

EXAMPLE 9-1

PHARMACEUTICAL COMPOSITION FOR PARENTERAL ADMINISTRATION, CONTAINING DONEPEZIL

CROSS-REFERENCE TO RELATED APPLICATIONS

This application is a national phase application of PCT Application No. PCT/KR2014/002844, filed on 2 Apr. 2014, which claims benefit of Korean Patent Application 10-2013-0036292, filed on 3 Apr. 2013. The entire disclosure of the application identified in this paragraph is incorporated herein by reference.

FIELD

The present invention relates to a composition for parenteral administration comprising donepezil as an active ingredient and a preparation method therefor. In the present invention, donepezil—which has been conventionally used for oral or transdermal dosage form—is prepared as microspheres comprising a biodegradable, biocompatible polymer and a controlled release agent so that a sustained-release pharmaceutical composition for parenteral administration is provided. As a result, effects of reducing the frequency of administration to a patient and maintaining effective concentration in the blood for a long time by sustained release in the body for 2-12 weeks or more can be obtained.

BACKGROUND

Recently, as the number of patients with Alzheimer's-type dementia has increased along with the growth of the elderly population, patient care has emerged as a serious social problem, and anti-dementia drugs have been developed rapidly. Donepezil hydrochloride having inhibitory effect on acetylcholine esterase has been widely used as a therapeutic agent for Alzheimer's disease, and most of anti-dementia drugs are orally administered in tablet form. Drugs are administered to patients not only in the form of tablet, capsule, syrup and granules but also by injection, rectal administration, transdermal administration and the like with the proper selection according to the properties of diseases or drugs. However, it is difficult to orally administer anti-dementia drugs to patients suffering from the progression of dementia.

To improve convenience and compliance of patients by reducing the frequency of taking drugs and maintain the concentration of drugs continuously for a long time, it is believed that sustained-release injections are very useful. However, in the case of administering anti-dementia drugs to patients for a long time—for example, 4 weeks or more—it is difficult to make drugs be continuously and uniformly released while maintaining biological activities of drugs in the body. Accordingly, the need has grown for sustained-release injection of an anti-dementia drug having a property of stable drug release for a long time.

As for the prescription pattern of oral dosage form of donepezil hydrochloride, the usual prescription is first 5 mg of donepezil hydrochloride administered once a day at bedtime. This dose is used for 4-6 weeks, and donepezil hydrochloride is then increased to 10 mg and administered once a day. In the case of the first time patient in whom the treatment is carried out in such a manner, there is a shortcoming that drug compliance to daily oral administration is low. As a result, there has been a need to develop sustained-release preparations. However, there has been no report about development of donepezil as a sustained-release injection.

As an example of sustained-release preparation, Pengcheng Zhang et al. prepared sustained-release microparticles of donepezil and evaluated them (Pengcheng Zhang, Lingli Chen, Wangwen Gu, Zhenghong Xu, Yu Gao, Yaping Li, In vitro and in vivo evaluation of donepezil-sustained release microparticles for the treatment of Alzheimer's disease, *Biomaterials*, 28 (2007) 1882~1888). They prepared microparticles containing donepezil by the use of copolymer of lactide and glycolide, but the content of donepezil in microparticles was about 13.2% and the loading rate was only 66%, so that there was much drug loss and a problem that too much administration amount was needed for practical application to patients.

As such, there has been a need for developing a sustained-release parenteral preparation of donepezil which is not administered in a large amount, has stable drug-releasing property for a long time and continuously maintains an effective concentration in the blood.

DISCLOSURE OF INVENTION

Technical Problem

The present invention is for improving drug compliance of donepezil. The object of the present invention is the provision of sustained-release preparation for parenteral administration having stable drug-releasing property for a long time by preparing donepezil as microspheres along with a biocompatible polymer and a controlled release agent.

Solution to Problem

To accomplish the above object, the present invention provides a donepezil microsphere comprising a biodegradable, biocompatible polymer, which comprises donepezil or a pharmaceutically acceptable salt thereof, wherein the content of donepezil is 15% by weight or more.

The donepezil microsphere of the present invention may further comprise a poorly soluble salt of donepezil as a controlled release agent. The example of poorly soluble salt is, but is not limited to, xinafoate, napadisilate or pamoate.

In the donepezil microsphere of the present invention, the biodegradable, biocompatible polymer may have the intrinsic viscosity of 0.5 to 1.9 dL/g. The example of the biodegradable, biocompatible polymer is, but is not limited to, poly(lactide-co-glycolide), polylactide, polyglycolide, polycaprolactone, gelatin, hyaluronate or a mixture thereof, and preferably at least one of polyglycolide, polylactide, and a copolymer of polyglycolide and polylactide. Specifically, in the case of copolymer of polyglycolide and polylactide, the molar ratio of lactide to glycolide is preferably 50:50 to 90:10, and most preferably 85:15.

The donepezil microsphere of the present invention may have the size (D50) of 10 to 200 μm. The content of donepezil in the microsphere is preferably 15 to 50% by weight. If the content of donepezil in the microsphere is less than 15% by weight, the amount of microsphere to be administered is so large that it may be problematic in lowering drug compliance. If the content of donepezil in the microsphere is greater than 50% by weight, fast drug release may cause a problem wherein sufficient sustained-release effect cannot be obtained.

In the donepezil microsphere of the present invention, release of donepezil may continue for 2 to 12 weeks or more.

To accomplish another object, the present invention provides a method for preparing donepezil microsphere which comprises the steps of:

dissolving donepezil or a pharmaceutically acceptable salt thereof and a biodegradable, biocompatible polymer in one or more solvents;

forming a microsphere by adding the solution of donepezil and biodegradable, biocompatible polymer to a hydrophilic polymer aqueous solution and agitating; and removing the solvent.

In the method for preparing donepezil microsphere of the present invention, if necessary, a step of washing the microsphere with a solvent such as ethanol may be further comprised. By this means, initial burst release of donepezil may be suppressed.

In addition, the present invention provides a pharmaceutical composition for parenteral administration comprising a donepezil microsphere comprising donepezil or a pharmaceutically acceptable salt thereof, and a pharmaceutically acceptable carrier. Specifically, it is preferable that the pharmaceutical composition for parenteral administration is an injection.

The pharmaceutical composition comprising donepezil or a pharmaceutically acceptable salt thereof of the present invention may be used as a therapeutic agent for Alzheimer's-type dementia. Administration dose may be variously adjusted according to the age of patients, symptom, dosage form and the like. Donepezil may be administered at a dose of 2.0 to 15.0 mg/day, and preferably 5.0 to 10.0 mg/day.

The donepezil microsphere of the present invention may be provided as a preparation in which the donepezil microsphere is suspended in an injectable suspending agent at the time of final administration. The injectable suspending agent is a water-soluble organic carrier, and its example includes, but is not limited to, an isotonic agent, a thickening agent, a surfactant and a buffer. Examples of available isotonic agent are, but are not limited to, a water-soluble excipient such as mannitol, sucrose, sorbitol, trehalose, lactose, sodium chloride, or sugars. Examples of thickening agent are, but are not limited to, carmellose sodium, sodium carboxymethyl cellulose or povidone. Examples of surfactant are, but are not limited to, polyoxyethylene sorbitans such as Polysorbate 80 or Polysorbate 20, or sorbitan esters such as Span 80 or Span 20. In addition, examples of buffer are, but are not limited to, sodium monohydrogen phosphate, anhydrous citric acid, sodium hydroxide or sodium chloride.

Effects

The donepezil microsphere according to the present invention has stable drug releasing property for a long time so that donepezil can be maintained at an effective concentration in the blood for 2 to 12 weeks or more. As a result, in the case of preparing as a parenteral preparation such as injection, it is safe and shows continuous effect, thereby improving drug compliance of patients.

MODE FOR THE INVENTION

Figure 1A:
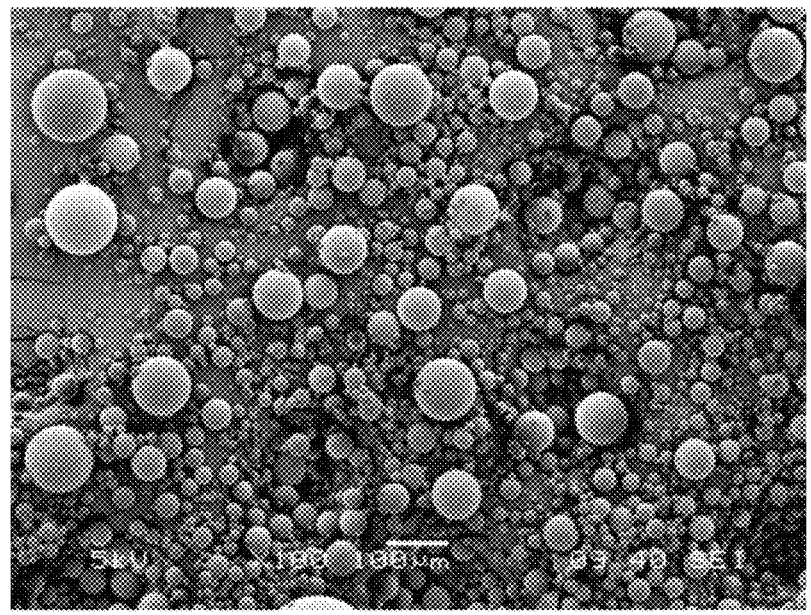
FIG. 1 is photographs showing SEM analysis results for the morphology of donepezil microspheres of each example.
Figure 1B:
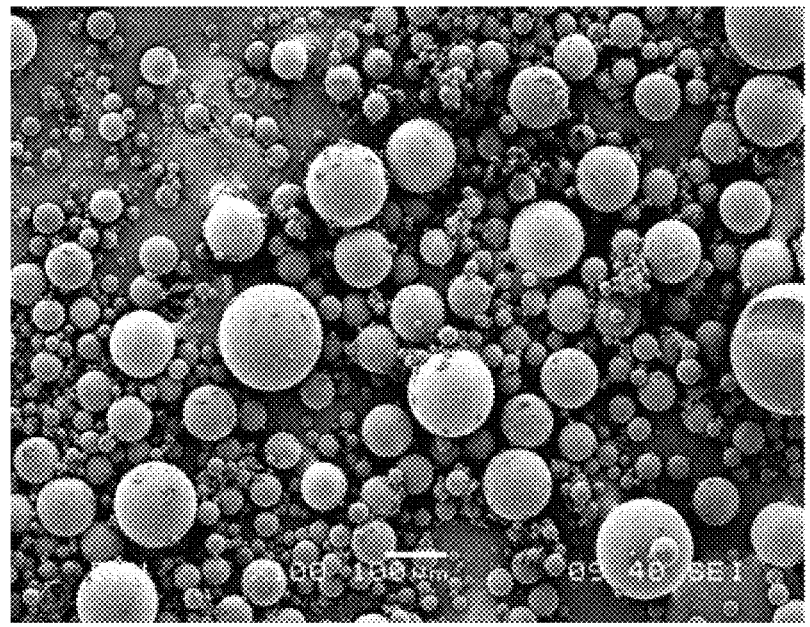
Figure 1C:
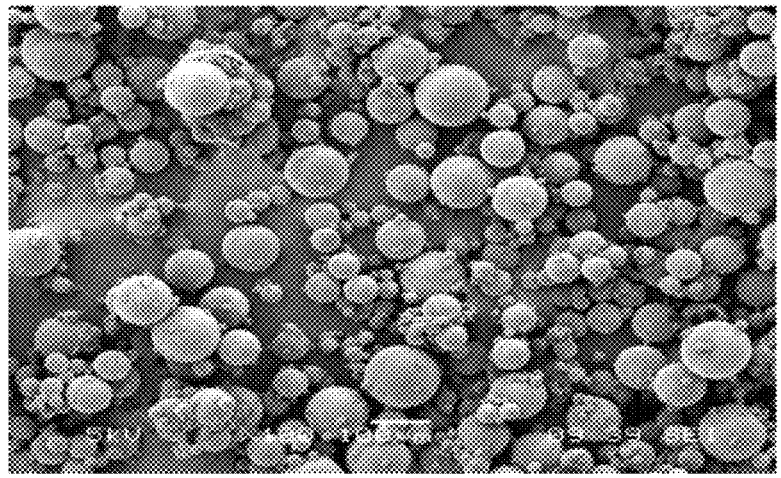
Figure 1D:
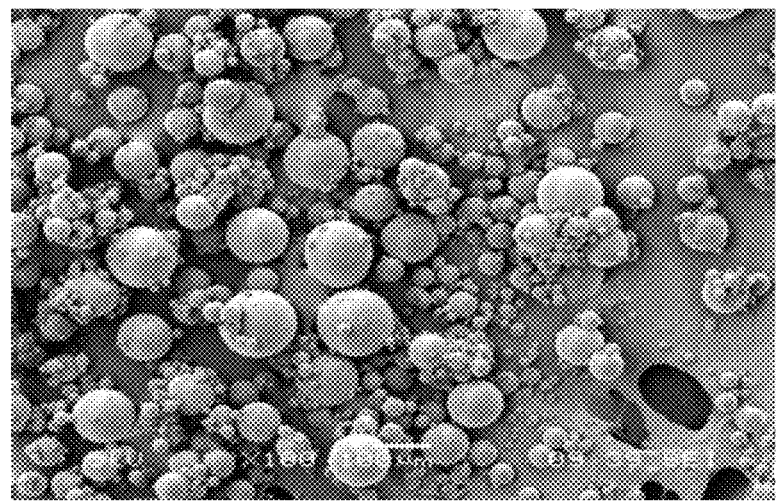
Figure 1E:
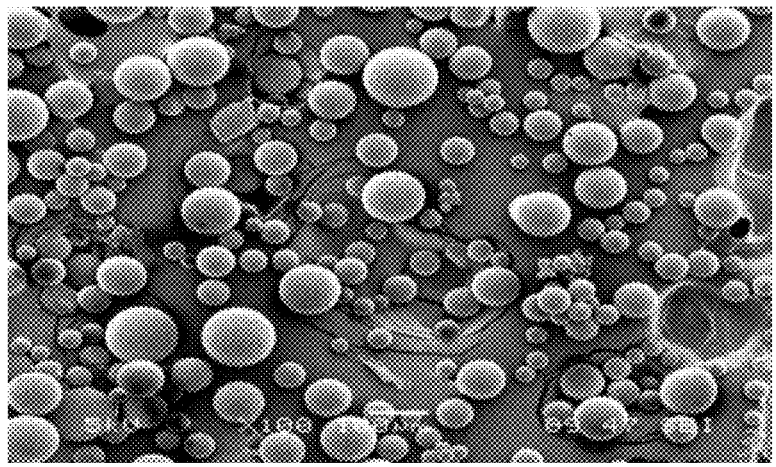
Figure 1F:
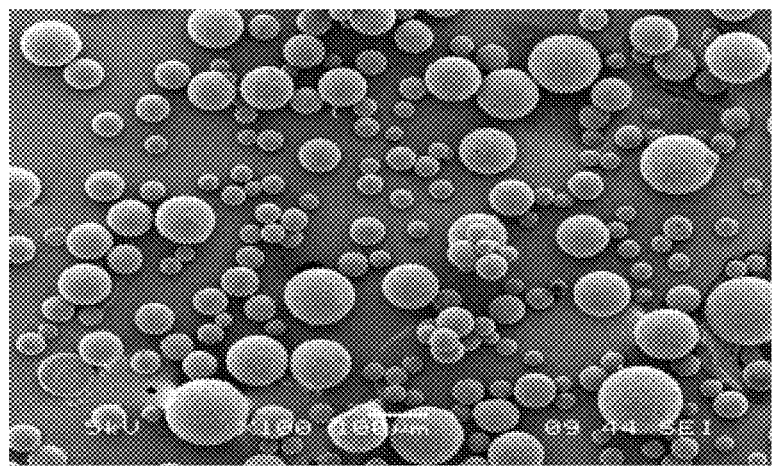
Figure 1G:
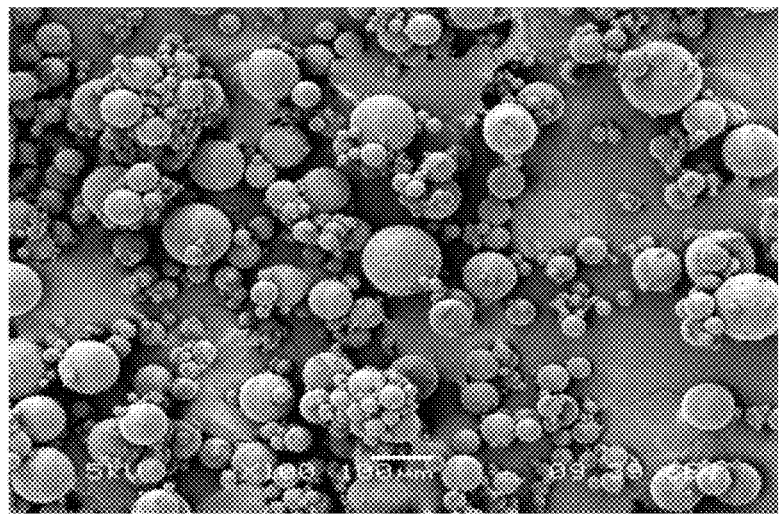
Figure 1H:
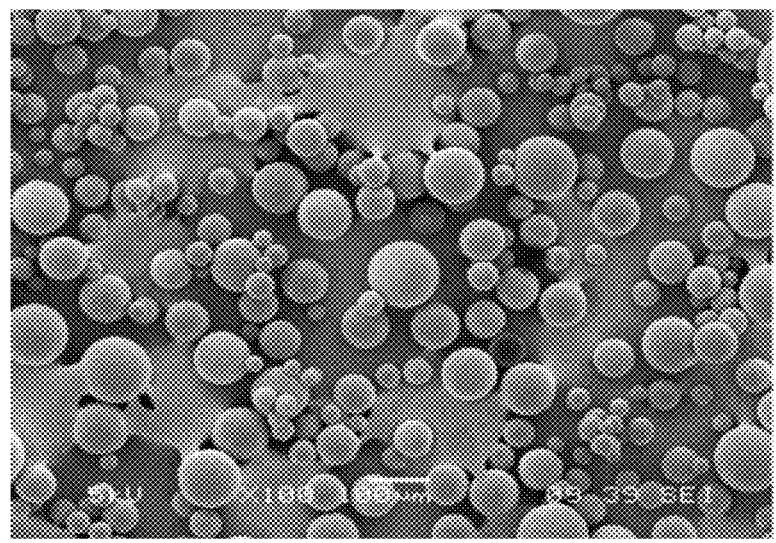
Figure 1I:
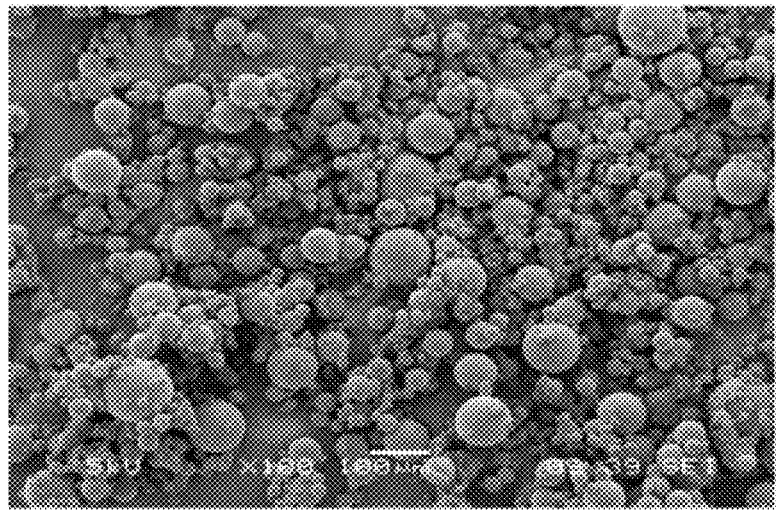
Figure 1J:
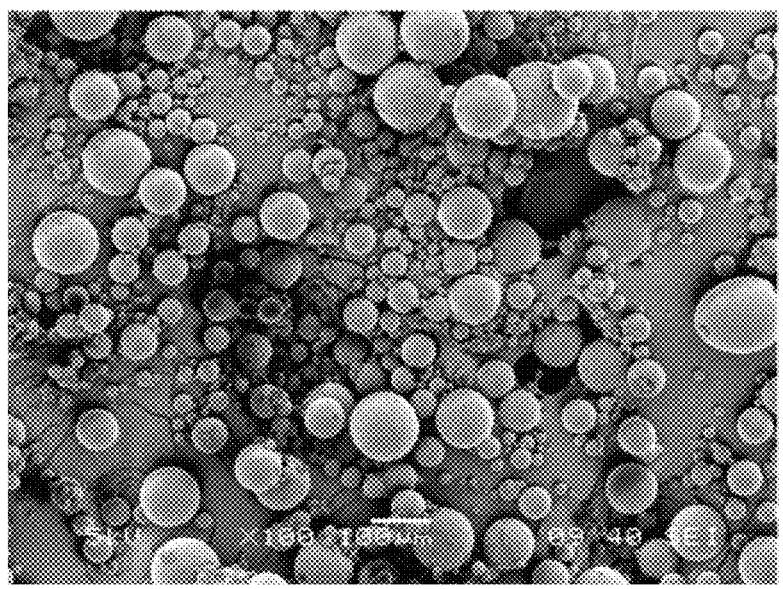
Figure 1K:
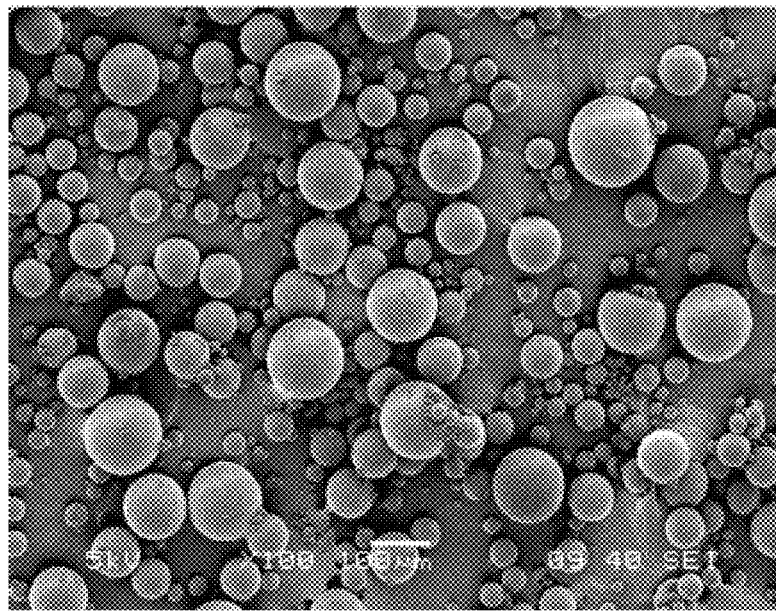
Figure 1L:
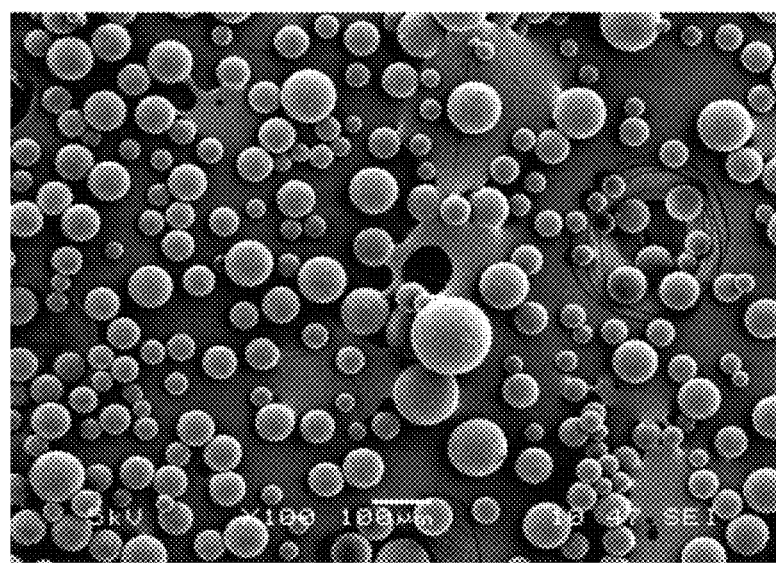
Figure 1M:
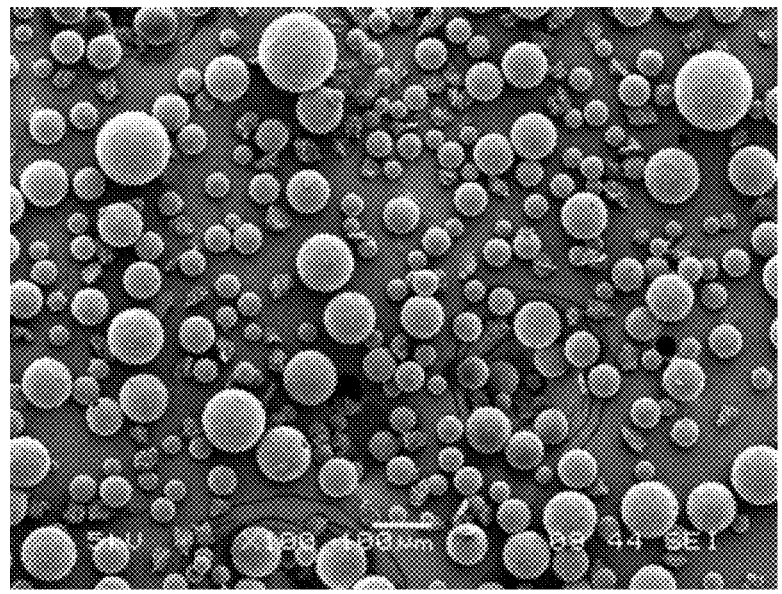
Figure 2A:
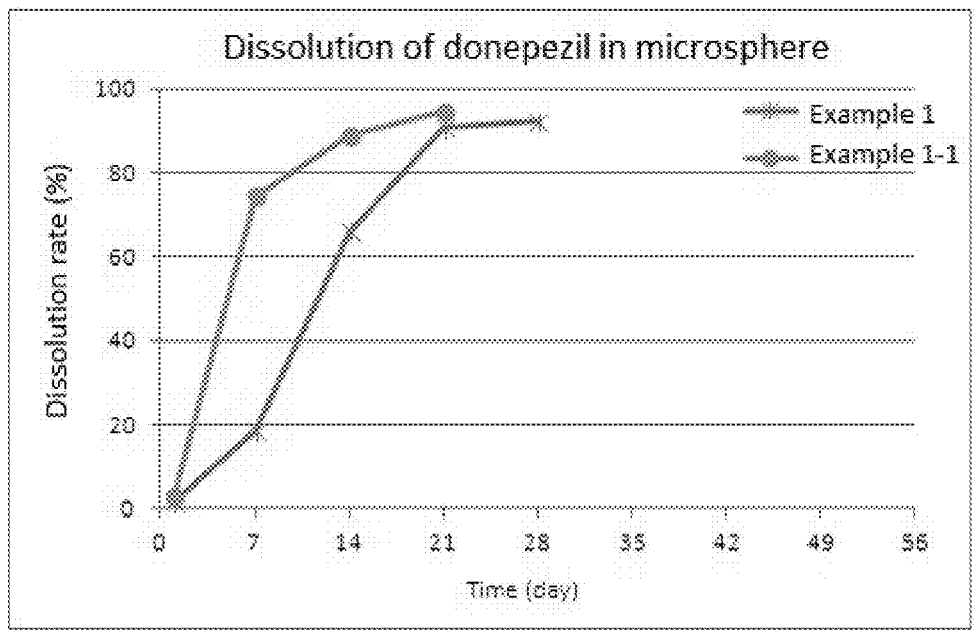
FIG. 2 is graphs representing the dissolution rate of donepezil microspheres of each example according to time.
Figure 2B:
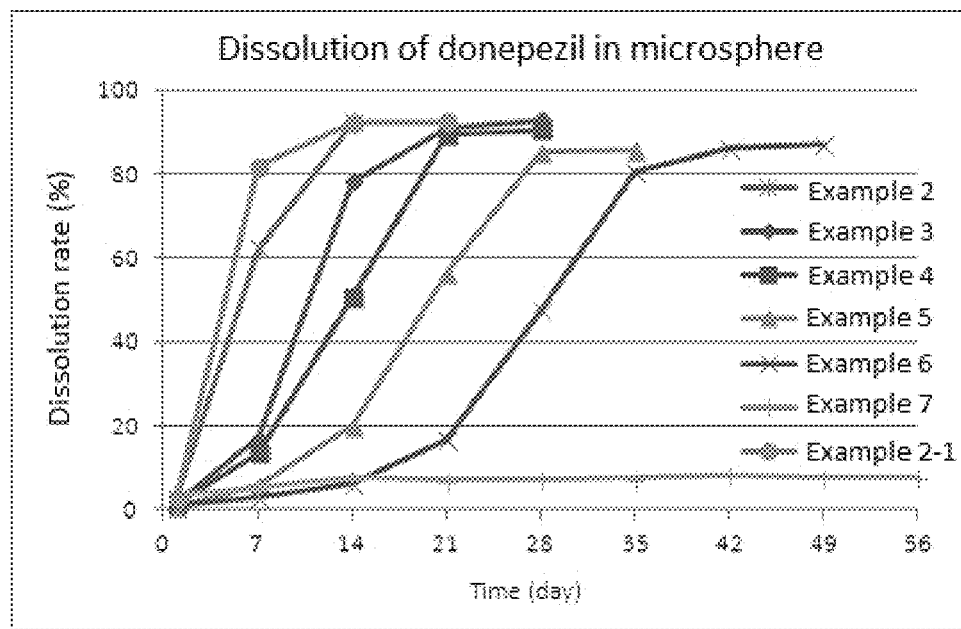
Figure 2C:
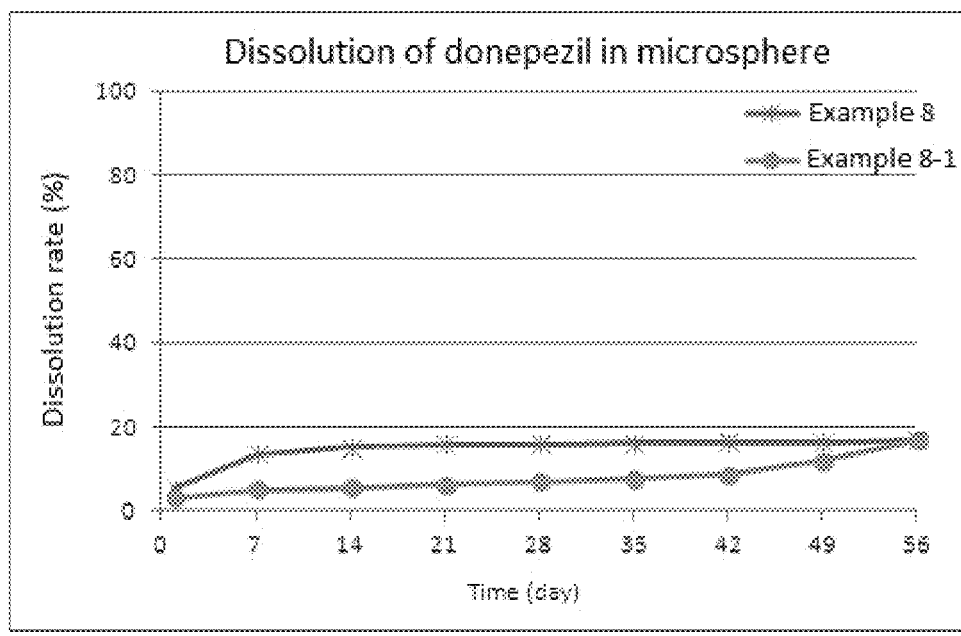
Figure 2D:
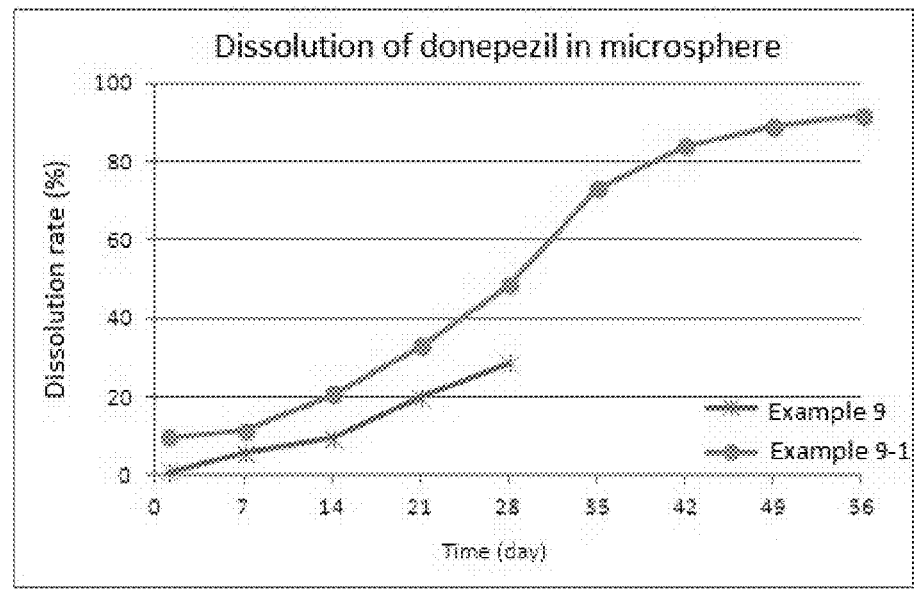

Hereinafter, the present invention is explained in more detail with the following examples. However, the following examples are only intended to facilitate understanding of the present invention, and the protection scope of the present invention is not limited thereto.

Example 1: Preparation of Donepezil Microspheres 12.6 g of methylene chloride (Merck) was added to 1.4 g of biocompatible polymer (RESOMER RG 858S, Boehringer Ingelheim) and 0.6 g of donepezil base (Megafine, India), and the mixture was completely dissolved by agitation to obtain a dispersion solution.

500 ml of 0.5% polyvinyl alcohol (Mn=30,000-70,000; Sigma) aqueous solution was added to a reactor for preparing microspheres and the temperature was set at 10° C., and the obtained dispersion solution was then slowly added thereto by the use of a syringe with the agitation of 3,000 rpm to prepare microspheres. Next, the temperature was increased to volatilize organic solvents for 2 hours and then cooled to 10° C. for 1 hour.

The prepared microspheres were washed with water for injection several times, and wet filtration was then carried out by the use of sieves having 25 μm and 150 μm sizes. The resultant was freeze-dried for 64 hours.

Example 1-1: Preparation of Microspheres

Microspheres were prepared according to the same method as in Example 1 except for the use of biocompatible polymer (RESOMER RG 757S, Boehringer Ingelheim).

Example 1-2: Preparation of Microspheres

Microspheres were prepared according to the same method as in Example 1 except that 12.6 g of methylene chloride (Merck) was added to 0.8 g of biocompatible polymer (RESOMER RG 858S, Boehringer Ingelheim) and 1.2 g of donepezil base (Megafine, India), and completely dissolved by agitation to obtain a dispersion solution.

Examples 2 to 7: Preparation of Microspheres According to Ratio of Controlled Release Agent (Xinafoic Acid)

1.2 g of biocompatible polymer (RESOMER RG 858S, Boehringer Ingelheim), 0.8 g of donepezil base (Megafine, India) and 0.1-1.0 equivalent of 1-hydroxy-2-naphtholic acid (xinafoic acid, Sigma Aldrich) as a controlled release agent with respect to donepezil were added, and 10.8 g of methylene chloride (Merck) was then added thereto. The mixture was completely dissolved by agitation to obtain a dispersion solution.

500 ml of 0.5% polyvinyl alcohol (Mn=30,000-70,000; Sigma) aqueous solution was added to a reactor for preparing microspheres and the temperature was set at 10° C., and the obtained dispersion solution was then slowly added thereto by the use of a syringe with the agitation of 3,000 rpm to prepare microspheres. Next, the temperature was increased to volatilize organic solvents for 2 hours and then cooled to 10° C. for 1 hour.

The prepared microspheres were washed with water for injection several times, and wet filtration was then carried out by the use of sieves having 25 μm and 150 μm sizes. The resultant was freeze-dried for 64 hours.

Table 1 represents the equivalent of xinafoic acid with respect to donepezil base used in Examples 2 to 7.

TABLE 1

| Example | Equivalent of xinafoic acid with respect to donepezil base (eq) |
|---|---|
| Example 2 | 0.1 |
| Example 3 | 0.25 |
| Example 4 | 0.3 |
| Example 5 | 0.4 |
| Example 6 | 0.5 |
| Example 7 | 1.0 |

Example 2-1: Preparation of Microspheres

Microspheres were prepared according to the same method as in Example 2 except that a controlled release agent was not used.

Example 8: Preparation of Microspheres by Use of Donepezil Xinafoate 9.0 g of methylene chloride (Merck) was added to 1.0 g of biocompatible polymer (RESOMER RG 858S, Boehringer Ingelheim) and 1.0 g of donepezil xinafoate (33.3% [w/w] to the total weight of solid as donepezil base), and the mixture was completely dissolved by agitation to obtain a dispersion solution.

500 ml of 0.5% polyvinyl alcohol (Mn=30,000-70,000; Sigma) aqueous solution was added to a reactor for preparing microspheres and the temperature was set at 10° C., and the obtained dispersion solution was then slowly added thereto by the use of a syringe with the agitation of 3,000 rpm to prepare microspheres. Next, the temperature was increased to volatilize organic solvents for 2 hours and then cooled to 10° C. for 1 hour.

The prepared microspheres were washed with water for injection several times, and wet filtration was then carried out by the use of sieves having 25 μm and 150 μm sizes. The resultant was freeze-dried for 64 hours.

Example 8-1: Preparation of Microspheres

Microspheres were prepared according to the same method as in Example 8 except that 1.0 equivalent of xinafoic acid as a controlled release agent with respect to donepezil base was added.

Example 8-2: Preparation of Microspheres by Use of Donepezil Pamoate 9.0 g of methylene chloride (Merck) was added to 0.65 g of biocompatible polymer (RESOMER RG 858S, Boehringer Ingelheim) and 1.35 g of donepezil pamoate (33.3% [w/w] to the total weight of solid as donepezil base), and the mixture was completely dissolved by agitation to obtain a dispersion solution.

500 ml of 0.5% polyvinyl alcohol (Mn=30,000-70,000; Sigma) aqueous solution was added to a reactor for preparing microspheres and the temperature was set at 10° C., and the obtained dispersion solution was then slowly added thereto by the use of a syringe with the agitation of 3,000 rpm to prepare microspheres. Next, the temperature was increased to volatilize organic solvents for 2 hours and then cooled to 10° C. for 1 hour.

The prepared microspheres were washed with water for injection several times, and wet filtration was then carried out by the use of sieves having 25 μm and 150 μm sizes. The resultant was freeze-dried for 64 hours.

Example 8-3: Preparation of Microspheres by Use of Donepezil Napadisilate 9.0 g of methylene chloride (Merck) was added to 0.83 g of biocompatible polymer (RESOMER RG 858S, Boehringer Ingelheim) and 1.17 g of donepezil napadisilate (33.3% [w/w] to the total weight of solid as donepezil base), and the mixture was completely dissolved by agitation to obtain a dispersion solution.

500 ml of 0.5% polyvinyl alcohol (Mn=30,000-70,000; Sigma) aqueous solution was added to a reactor for preparing microspheres and the temperature was set at 10° C., and the obtained dispersion solution was then slowly added thereto by the use of a syringe with the agitation of 3,000 rpm to prepare microspheres. Next, the temperature was increased to volatilize organic solvents for 2 hours and then cooled to 10° C. for 1 hour.

The prepared microspheres were washed with water for injection several times, and wet filtration was then carried out by the use of sieves having 25 μm and 150 μm sizes. The resultant was freeze-dried for 64 hours.

Example 9: Preparation of Microspheres for Suppressing Initial Burst Release 2.85 g of biocompatible polymer (RESOMER RG 858S, Boehringer Ingelheim), 2.15 g of donepezil base (Megafine, India) and 0.6 equivalent (644 mg) of 1-hydroxy-2-naphtholic acid (xinafoic acid, Sigma Aldrich) as a controlled release agent with respect to donepezil were added, and 25.65 g of methylene chloride (Merck) was then added thereto. The mixture was completely dissolved by agitation to obtain a dispersion solution.

The obtained dispersion solution was then slowly added to 0.5% polyvinyl alcohol (Mn=30,000-70,000; Sigma) aqueous solution in a L4R mixer (Silverson, United Kingdom) which was set at 10° C. by the use of an in-line unit with the agitation of 3,000 rpm to prepare microspheres. Next, the temperature was increased to volatilize organic solvents for 3 hours and then cooled to 10° C. for 1 hour.

The prepared microspheres were washed with water for injection several times, and the first wet filtration was then carried out by the use of sieves having the size of 25 μm. The obtained microspheres were washed with 25% (w/w) ethanol aqueous solution at 20° C. for 10 minutes, and the second wet filtration was then carried out by the use of sieves having 25 μm and 150 μm sizes. The resultant was freeze-dried for 64 hours.

Example 9-1: Preparation of Microspheres

Microspheres were prepared according to the same method as in Example 9 except for the ethanol-washing step.

Experimental Example 1: Observation of Microsphere Morphology

To observe the surface of the microspheres, about 10 mg of the microspheres were fixed on an aluminum stub and coated with platinum under 0.1 torr of degree of vacuum and high voltage (10 kV) for 3 minutes. The microspheres were installed on a scanning electron microscope (SEM) (Hitachi S-4800 FE-SEM), and then the surface of the microspheres was observed by using an image-analysis program.

FIG. 1 is photographs showing SEM analysis results for the morphology of donepezil microspheres of each example. FIG. 1a is an SEM photograph of microspheres prepared in Example 1, FIG. 1b is that of Example 1-1, FIGS. 1c to 1h are those of Examples 2 to 7, FIG. 1i is that of Example 2-1, FIGS. 1j and 1k are those of Examples 8 and 8-1, and FIGS. 1l and 1m are those of Examples 9 and 9-1, respectively.

As confirmed by FIGS. 1a to 1m, the size of the donepezil microspheres prepared in the Examples was within the range of 10 to 200 μm, and they were globular in shape.

Experimental Example 2: Measurement of Content and Loading Rate of Donepezil

About 50 mg of the microspheres were completely dissolved in a mobile phase and filtrated with a 0.45 μm syringe filter to obtain a test solution. The content of donepezil loaded into the microspheres was measured by HPLC under the following conditions:

Column: Inertsil ODS 2, C18 5 μm, 4.5×150 mm
Loading amount: 20 μl
Detection wavelength: 271 nm
Mobile phase: phosphate buffered saline:acetonitrile=60:40 (pH 5.0)
The results are represented in Table 2.

TABLE 2

|  | Drug content (%) | Drug loading rate (%) |
|---|---|---|
| Example 1 | 28.0 | 93.3 |
| Example 1-1 | 27.5 | 91.7 |
| Example 1-2 | 57.1 | 95.0 |
| Example 2 | 35.0 | 89.5 |
| Example 2-1 | 35.6 | 89.0 |
| Example 3 | 32.8 | 86.1 |
| Example 4 | 35.2 | 93.1 |
| Example 5 | 34.5 | 93.0 |
| Example 6 | 32.0 | 88.2 |
| Example 7 | 30.4 | 91.3 |
| Example 8 | 30.5 | 91.6 |
| Example 8-1 | 31.1 | 94.2 |
| Example 8-2 | 29.4 | 85.4 |
| Example 8-3 | 30.5 | 83.8 |
| Example 9 | 35.7 | 93.7 |
| Example 9-1 | 36.1 | 94.7 |

As can be seen from Table 2, in all donepezil microspheres prepared in the Examples the content of donepezil in the microspheres was 15% by weight or more. As a result, it can be known that about 85% or more of donepezil based on the initial addition amount is sufficiently loaded into the microsphere.

Experimental Example 3: In Vitro Long-Term Dissolution Test of Microspheres

After placing about 20 mg of the microspheres prepared in the Examples into a 200 ml test tube, HEPES solution (pH 7.4) was added thereto and incubated in a 37.0° C. water bath. Supernatant was taken at regular intervals to measure the dissolution rate of donepezil by HPLC. Table 3 and FIG. 2 represent the dissolution rate of donepezil microspheres according to time.

TABLE 3

|  | Donepezil Dissolution Rate (%) | | | | | | | | |
|---|---|---|---|---|---|---|---|---|---|
|  | Day 1 | Day 7 | Day 14 | Day 21 | Day 28 | Day 35 | Day 42 | Day 49 | Day 56 |
| Example 1 | 2.4 | 18.7 | 66.0 | 90.7 | 92.0 | — | — | | |
| Example 1-1 | 3.6 | 74.5 | 88.9 | 94.6 | — | | | | |
| Example 1-2 | 13.5 | 87.5 | | | | | | | |
| Example 2 | 3.7 | 62.1 | 92.3 | — | | | | | |
| Example 3 | 2.8 | 17.1 | 78.2 | 91.0 | 92.8 | — | | | |
| Example 4 | 1.5 | 13.5 | 50.7 | 89.4 | 90.4 | — | | | |
| Example 5 | 1.8 | 5.7 | 20.0 | 56.3 | 85.1 | 85.4 | — | | |
| Example 6 | 2.2 | 3.0 | 6.2 | 16.8 | 47.6 | 80.6 | 85.9 | 86.9 | — |
| Example 7 | 4.4 | 5.2 | 7.6 | 7.2 | 7.3 | 7.6 | 8.4 | 7.7 | 7.8 |
| Example 2-1 | 4.1 | 81.8 | 92.1 | 92.4 | — | | | | |
| Example 8 | 5.2 | 13.5 | 15.1 | 15.8 | 15.9 | 16.2 | 16.3 | 16.4 | 16.8 |
| Example 8-1 | 4.2 | 4.9 | 5.5 | 6.3 | 6.8 | 7.6 | 8.6 | 11.8 | 16.7 |
| Example 8-2 | 5.6 | 10.3 | 13.5 | 18.3 | 20.9 | 24.8 | 27.0 | 30.4 | 32.3 |
| Example 8-3 | 4.9 | 8.1 | 10.3 | 11.8 | 13.1 | 15.6 | 17.4 | 19.4 | 20.8 |
| Example 9 | 0.8 | 5.8 | 9.4 | 20.1 | 28.7 | | | | |
| Example 9-1 | 9.7 | 11.4 | 20.6 | 32.8 | 48.4 | 73.0 | 83.8 | 88.7 | 91.8 |

As can be seen from Table 3 and FIG. 2, it can be known that in the case of the microspheres prepared in Examples 1 and 1-1 the release rate of the drug was decreased when the viscosity of the polymer and the ratio of lactide were high. As such, the release rate of the drug can be controlled by adjusting the ratio of lactide to glycolide in copolymer of polyglycolide and polylactide. Meanwhile, in the case of the microspheres prepared in Example 1-2 in which the drug content is as high as 57.1%, it was confirmed that the dissolution of the drug is fast.

In addition, from the results of Examples 2 to 7 and 2-1, it can be known that the dissolution rate of the drug was retarded according to the increase of xinafoic acid concentration. The dissolution rate of the drug in the microspheres prepared by the use of synthesized donepezil xinafoate (Example 8) was almost identical to that in the microspheres prepared by adding xinafoic acid to donepezil base (Example 8-1). In addition, sustained release was confirmed in the microspheres prepared by the use of pamoate and napadisilate as poorly soluble salts of donepezil (Examples 8-2 and 8-3).

Meanwhile, in Example 9 ethanol washing of microspheres was carried out to suppress initial burst release of the drug. As a result, it was confirmed that initial burst release of the drug was considerably suppressed as compared with Example 9-1 in which ethanol washing was not carried out.

Experimental Example 4: Residual Solvent Test of Microspheres

After placing about 100 mg of the microspheres into a GC vial, 10 ml of internal standard solution was added thereto and dissolved. Then, residual solvents were measured by the use of GC. The column used for this measurement was charged with G25 type, the internal diameter was 25 m×0.32 mm, the film thickness was 0.5 µm, the loading amount was 1 µl, and the measurement was carried out by the use of a flame ionization detector at 250° C.

Table 4 represents the results for the amount of residual solvents of donepezil microspheres prepared in each Example.

TABLE 4

|  | Methylene chloride (ppm) | Ethanol (ppm) |
| --- | --- | --- |
| Example 1 | 68 | — |
| Example 2 | 34 | — |
| Example 3 | 66 | — |
| Example 4 | 59 | — |
| Example 5 | 98 | — |
| Example 6 | 71 | — |
| Example 7 | 83 | — |
| Example 8 | 73 | — |
| Example 9 | N/D | 621 |
| Example 1-1 | 77 | — |
| Example 2-1 | 66 | — |
| Example 8-1 | 96 | — |
| Example 9-1 | 74 | — |

(N/D: Not Detected)

As can be seen from Table 4, it was confirmed that the donepezil microspheres prepared according to the present invention were under the residual solvent standards which are 600 ppm or less of methylene chloride and 5,000 ppm or less of ethanol.

Experimental Example 5: Analysis for Blood Drug Concentration

The microspheres prepared in each Example and commercially available preparation were diluted in 0.5 ml of suspension solution, and donepezil (900 µg/kg) was injected intramuscularly (I.M.) into rats. About 0.5 ml of blood samples were collected at predetermined times, pre-treated, and the concentration of donepezil was measured by the use of LC/MS/MS. FIG. 3 represents the measured results.

FIG. 3 is graphs representing the blood drug concentration according to time when the suspension of donepezil microspheres of each example is administered into the body.

Figure 3A:
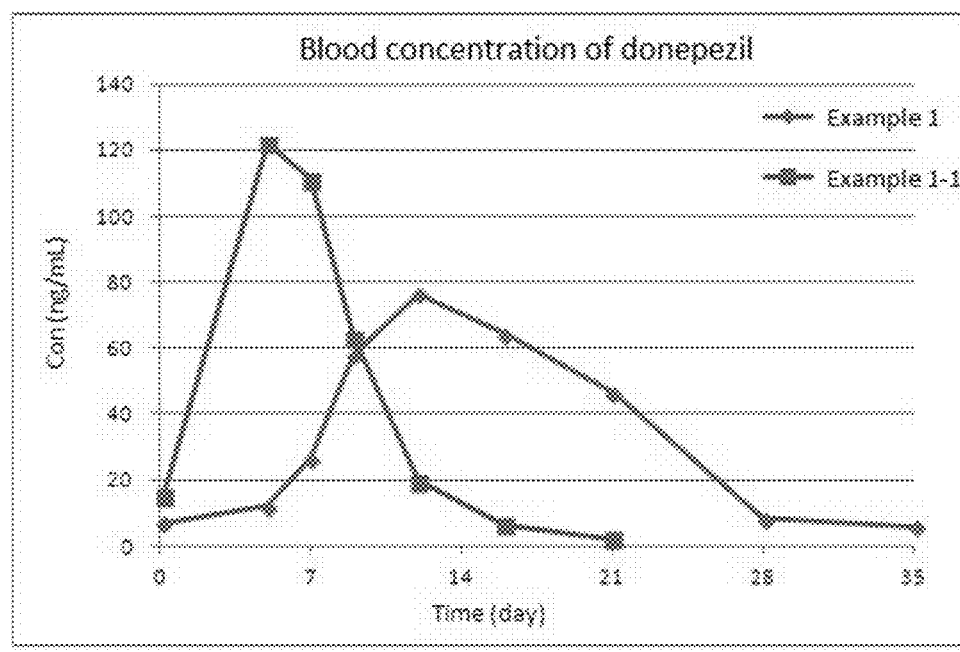
FIG. 3 is graphs representing the blood drug concentration according to time when the suspension of donepezil microspheres of each example is administered into the body.
Figure 3B:
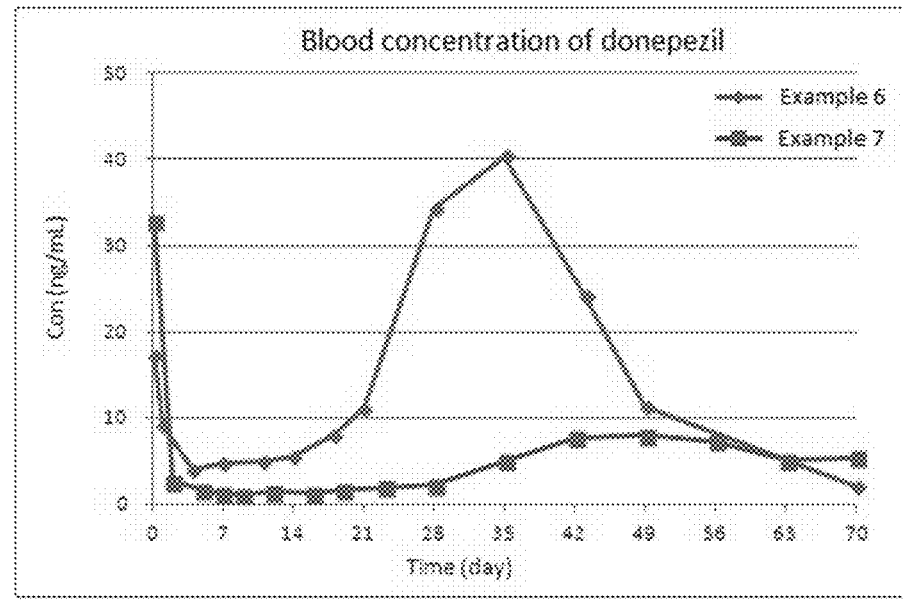
Figure 3C:
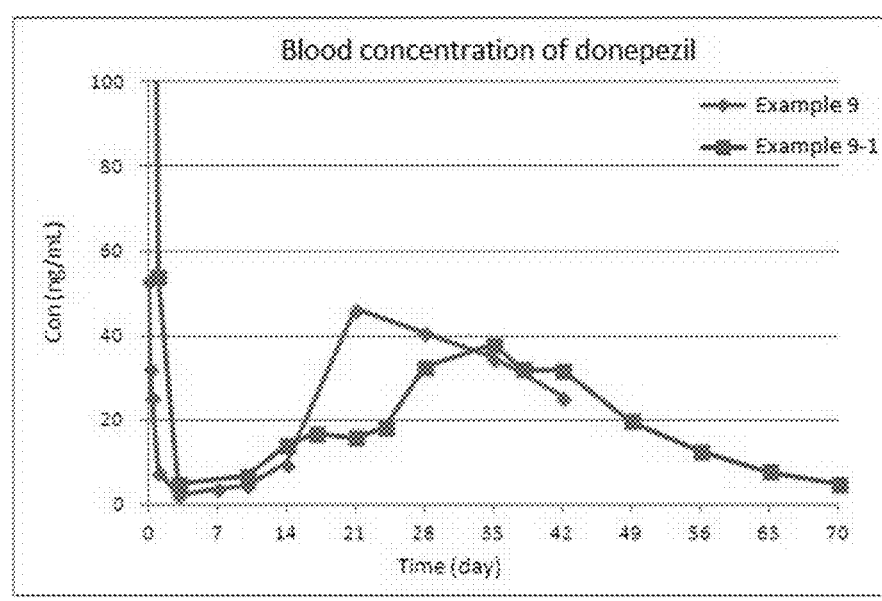

From FIG. 3a, it can be confirmed that in the case of microspheres prepared in Examples 1 and 1-1 the blood drug concentration was maintained steadily by decreasing the release rate of the drug when the viscosity of the polymer and the ratio of lactide were high. In addition, as can be seen from FIG. 3b, in the microspheres of Example 7 in which the concentration of xinafoic acid to donepezil base is twice as much as in Example 6, the blood drug concentration was maintained steadily by retarding the dissolution of donepezil. In FIG. 3c, it can be confirmed that in the microspheres of Example 9 in which ethanol washing of microspheres was carried out, the initial blood drug concentration was kept low.

Preparation Example 1: Preparation of Injection

Preparation of diluent: 500 mg of mannitol, 50 mg of sodium carboxymethyl cellulose and 10 mg of polysorbate 80 were dissolved in water for injection to make 10 ml, and sodium hydroxide was then added thereto to adjust pH to 7.0.

At the time of administering into patients, 2 ml of the above diluent was added to a vial in which 150-450 mg of donepezil was charged and suspended for injection.

What is claimed is:

1. A donepezil microsphere consisting essentially of a biodegradable, biocompatible polymer, donepezil, and a salt of donepezil,
   wherein the content of donepezil is 15% by weight or more;
   wherein the salt of donepezil is xinafoate or napadisilate; and
   wherein the biodegradable, biocompatible polymer is at least one selected from the group consisting of polyglycolide, polylactide, and a copolymer of polyglycolide and polylactide.

2. The donepezil microsphere according to claim 1, wherein the biodegradable, biocompatible polymer has an intrinsic viscosity of 0.5 to 1.9 dL/g.

3. The donepezil microsphere according to claim 1, wherein the biodegradable, biocompatible polymer is a copolymer of polyglycolide and polylactide, and the molar ratio of lactide to glycolide of the copolymer is 50:50 to 90:10.

4. The donepezil microsphere according to claim 3, wherein the biodegradable, biocompatible polymer is a copolymer of polyglycolide and polylactide, and the molar ratio of lactide to glycolide of the copolymer is 85:15.

5. The donepezil microsphere according to claim 1, which has a D50 size of 10 to 200 µm.

6. The donepezil microsphere according to claim 1, wherein the content of donepezil in the microsphere is 15 to 50% by weight.

7. The donepezil microsphere according to claim 1, wherein the microsphere releases donepezil for 2 to 12 weeks or more.

8. A method for preparing the donepezil microsphere according to claim 1, comprising:
   dissolving donepezil, a salt of donepezil, and a biodegradable, biocompatible polymer in one or more solvents to form a solution;
   forming a microsphere by adding the solution of donepezil, salt of donepezil and biodegradable, biocompatible polymer to a hydrophilic polymer aqueous solution and agitating; and
   removing the solvent,
   wherein the salt of donepezil is xinafoate or napadisilate; and
   the biodegradable, biocompatible polymer is at least one selected from the group consisting of polyglycolide, polylactide, and a copolymer of polyglycolide and polylactide.

9. The method according to claim 8, which further comprises washing the microsphere.

10. A pharmaceutical composition for parenteral administration comprising the donepezil microsphere according to claim 1 and a pharmaceutically acceptable carrier.

11. The pharmaceutical composition according to claim 10, which is an injection.

\* \* \* \* \*